United States Patent
Kraft et al.

(10) Patent No.: US 10,478,273 B2
(45) Date of Patent: Nov. 19, 2019

(54) DENTAL DEVICE FOR AUTOMATICALLY CLEANING A PERSON'S ORAL CAVITY

(71) Applicant: Daniel Kraft, Portola Valley, CA (US)

(72) Inventors: Daniel Kraft, Portola Valley, CA (US); Puneet Puri, Portola Valley, CA (US); Alexandr Borgul, Portola Valley, CA (US); Nagajyothi Nookula, Portola Valley, CA (US); Amr Sobhy, Portola Valley, CA (US); Sami Ben Hassine, Portola Valley, CA (US); Renato Stefani Augusto Silva, Portola Valley, CA (US)

( * ) Notice: Subject to any disclaimer, the term of this patent is extended or adjusted under 35 U.S.C. 154(b) by 658 days.

(21) Appl. No.: 14/912,310

(22) PCT Filed: Aug. 18, 2014

(86) PCT No.: PCT/US2014/051537
§ 371 (c)(1),
(2) Date: Feb. 16, 2016

(87) PCT Pub. No.: WO2015/024023
PCT Pub. Date: Feb. 19, 2015

(65) Prior Publication Data
US 2016/0206415 A1    Jul. 21, 2016

Related U.S. Application Data (60) Provisional application No. 61/866,966, filed on Aug. 16, 2013, provisional application No. 61/867,024, filed on Aug. 17, 2013.

(51) Int. Cl.
A61C 17/20    (2006.01)
A61C 17/22    (2006.01)
(Continued)

(52) U.S. Cl.
CPC ............ A61C 17/228 (2013.01); A46B 9/045 (2013.01); A46B 13/023 (2013.01);
(Continued)

(58) Field of Classification Search
CPC ..... A46B 9/045; A46B 15/0034; A46B 17/06; A61C 17/228; A61C 17/20; A61C 17/3481; A61C 17/36
See application file for complete search history.

(56) References Cited

U.S. PATENT DOCUMENTS 3,760,799 A    9/1973    Crowson ..................... 128/24 A
4,011,616 A    3/1977    Kennedy ....................... 15/21 R
(Continued)

FOREIGN PATENT DOCUMENTS

EP    1 506 746    2/2005    ............. A61C 17/02

OTHER PUBLICATIONS

European Office Action issued in application No. 14 836 528.1 dated Mar. 22, 2018 (4 pgs).
(Continued)

Primary Examiner — Randall E Chin
(74) Attorney, Agent, or Firm — Hayes Soloway P.C.

(57) ABSTRACT

Mouthpieces for fitting inside a user's mouth and cleaning the teeth, tongue, gums and/or roof of the mouth are provided. The mouthpiece is a hands free toothbrush designed to fit inside the mouth and clean the teeth, tongue, gums and/or roof of the mouth. The mouthpiece is made up of flexible material and is sized to fit the user's mouth. It contains intricately designed tube structures. It will clean the user's mouth, teeth, tongue and gums. The mouthpiece slips in to the mouth and fits or approximates the contour of an individual's teeth. When not in use, the mouthpiece can be kept in its own container for sanitary purposes.

13 Claims, 6 Drawing Sheets

(51) Int. Cl.
| | | |
|---|---|---|
| *A61C 17/34* | (2006.01) | |
| *A61C 17/36* | (2006.01) | |
| *A61C 17/32* | (2006.01) | |
| *A46B 9/04* | (2006.01) | |
| *A46B 13/02* | (2006.01) | |
| *A46B 15/00* | (2006.01) | |
| *A61C 19/06* | (2006.01) | |
| *A46B 17/06* | (2006.01) | |
| *A61B 5/01* | (2006.01) | |
| *A61B 5/145* | (2006.01) | |
| *A61B 5/00* | (2006.01) | |
| *A61C 17/06* | (2006.01) | |

(52) U.S. Cl.
CPC .......... *A46B 15/0034* (2013.01); *A46B 17/06* (2013.01); *A61B 5/01* (2013.01); *A61B 5/14503* (2013.01); *A61B 5/14539* (2013.01); *A61B 5/14542* (2013.01); *A61B 5/4875* (2013.01); *A61B 5/682* (2013.01); *A61C 17/04* (2013.01); *A61C 17/20* (2013.01); *A61C 17/32* (2013.01); *A61C 17/3481* (2013.01); *A61C 17/36* (2013.01); *A61C 19/063* (2013.01); *A61C 19/066* (2013.01); *A61B 2562/029* (2013.01)

(56) References Cited

U.S. PATENT DOCUMENTS

| | | | |
|---|---|---|---|
| 4,237,574 A * | 12/1980 | Kelly | A46B 9/045 |
| | | | 15/167.2 |
| 6,353,956 B1 | 3/2002 | Berge | 15/22.1 |
| 7,044,737 B2 | 5/2006 | Fu | 433/119 |
| 2005/0170316 A1* | 8/2005 | Russell | A46B 15/0002 |
| | | | 433/216 |
| 2007/0015112 A1 | 1/2007 | Hochman et al. | 433/215 |
| 2011/0072605 A1 | 3/2011 | Steur | 15/167.2 |
| 2011/0258792 A1 | 10/2011 | Steur et al. | 15/21.1 |
| 2012/0183919 A1 | 7/2012 | Levine | 433/29 |
| 2012/0295218 A1* | 11/2012 | Moll | A61C 17/0211 |
| | | | 433/32 |
| 2015/0044628 A1* | 2/2015 | Flyash | A61C 19/066 |
| | | | 433/27 |

OTHER PUBLICATIONS

Extended European Search Report issued in corresponding European Patent Appln. Serial No. 14836528.1 dated Feb. 3, 2017 (8 pgs).
International Search Report and Written Opinion issued in application No. PCT/US14/51537, dated Dec. 12, 2014 (8 pgs).
International Preliminary Report on Patentability issued in application No. PCT/US14/51537, dated Feb. 16, 2016 (6 pgs).

* cited by examiner

DENTAL DEVICE FOR AUTOMATICALLY CLEANING A PERSON'S ORAL CAVITY

The present invention relates to dental devices for cleaning a user's teeth, tongue, gums and/or roof of mouth. In particular, the invention relates to mouthpieces shaped to fit or approximate the contour of a user's teeth and designed for hands-free brushing.

Dental health is a very important, and often overlooked and/or improperly maintained, aspect of a person's overall health.

Oral hygiene is an important part of overall health, with poor brushing and flossing leading to high rates of gum disease, caries (cavities). Poor oral hygiene also has been shown to play a role in contributing to cardiovascular disease and inflammatory processes.

Conventional toothbrushes are handheld, which inherently introduces possibilities of user error and sub-optimal cleaning of the teeth. Moreover, conventional brushes are not particularly effective at cleaning between the teeth or at the gums, and thus a user should not only brush, but also floss as an additional step.

Moreover, the average individual does not "brush" their teeth for close to the recommendations, and even less floss on a regular basis. Tooth brush technology has evolved to include powered brushes and sonication based and augmented versions-however during brushing the brush element is generally only on one or two teeth at a time, and the overall "time on tooth" in any limited brushing is extremely limited. Analysis of mouth's and remaining plaque demonstrates significant levels left in average brushing situations.

The present disclosure provides hands-free toothbrushes, or mouthpieces, for fitting inside the mouth and cleaning a person's teeth, tongue, gums and/or roof of the mouth. The present disclosure further provides a supply unit for housing, cleaning and sterilizing mouthpieces. In one aspect, the present disclosure provides a mouthpiece that is a hands free toothbrush designed to fit inside the mouth and clean the teeth, tongue, gums and/or roof of the mouth. The mouthpiece is made up of flexible material and will come in different sizes. It contains intricately designed tube structures. It will clean the user's mouth, teeth and/or gums. The mouthpiece slips in to the mouth and fits or approximates the contour of an individual's teeth. When not in use, the mouthpiece can be kept in its own container for sanitary purposes.

In another aspect, the present disclosure provides a mouthpiece that includes ultrasonic transducers, which through the cavitation and decavitation effect kill bacteria, dislodge food, and clean the oral cavity (teeth and gums, helping to prevent plaque build up, and gum inflammation/infection). The mouthpiece also preferably contains an intricately designed tube structures. It will clean the user's mouth, teeth, tongue and/or gums. The mouthpiece slips in to the mouth and fits or approximates the contour of an individual's teeth. When not in use, the mouthpiece can be kept in its own container for sanitary purposes.

In another aspect, the present disclosure provides a mouthpiece having sensors for diagnosis and communication with the user. The mouthpiece is made up of flexible material and will come in different sizes. It contains an intricately designed tube structures. It will clean the user's mouth, teeth, tongue and/or gums. The mouthpiece slips in to the mouth and fits or approximates the contour of an individual's teeth. When not in use, the mouthpiece can be kept in its own container for sanitary purposes. It is a smart mouth piece containing sensors and bone conduction for diagnosis and communication with the user.

In another aspect, the present disclosure provides a mouthpiece having a vibration motor. The mouthpiece is a hands free toothbrush designed to fit inside the mouth and clean the teeth, tongue, gums and/or roof of the mouth. The mouthpiece is made up of flexible material and will come in different sizes. The mouthpiece includes bristles for brushing the user's teeth. The vibration motor in the mouthpiece transmits the vibrations to the bristles. The mouthpiece also preferably contains an intricately designed tube structures. It will clean the user's mouth, teeth and gums. The mouthpiece slips in to the mouth and fits or approximates the contour of an individual's teeth. When not in use, the mouthpiece can be kept in its own container for sanitary purposes.

In another aspect, the present disclosure provides a mouthpiece with an automatic flossing system. The mouthpiece is a hands free toothbrush designed to fit inside the mouth and clean the teeth, tongue, gums and/or roof of the mouth. The mouthpiece is made up of flexible material and will come in different sizes. The built-in flossing system in the mouthpiece provides an efficient way to remove interdental plaque and debris. The mouthpiece also preferably contains an intricately designed tube structures. It will clean the user's mouth and teeth. The mouthpiece slips in to the mouth and fits or approximates the contour of an individual's teeth. When not in use, the mouthpiece can be kept in its own container for sanitary purposes In yet another aspect, the present disclosure provides a supply unit for housing, cleaning and sterilizing a mouthpiece. The supply unit houses at least one mouthpiece. It contains the necessary sanitation equipment to clean and sterilize the mouth piece. The supply unit is also capable of self cleaning its output fluid tubes. It's a smart supply unit that displays and provides real time feedback to the user.

Further features and advantages of the present disclosure will be seen from the following description, taken in conjunction with the accompanying drawings, wherein like numerals depict like parts, and wherein.

The present disclosure provides hands-free toothbrushes, or mouthpieces, for fitting inside the mouth and cleaning a person's teeth, tongue, gums and/or roof of the mouth. The present disclosure further provides a supply unit for housing, cleaning and sterilizing mouthpieces.

Referring to FIGS. 1-6, the device 20 of the present disclosure comprises a mouthpiece 20 in the form of hands-free "toothbrush" designed to fit inside the mouth and clean the teeth, tongue, gums and/or roof of the mouth. Mouthpiece 20 may be formed of various sizes and shapes to fit the general population, but preferably is conformed to individual's mouth by using forming impressions on a rubbery substance using conventional dentistry techniques. Alternatively, a physical model may be produced by creating individual dental impressions using, for example a 3-D oral scanner. In yet another embodiment, mouthpiece 20 may comprise a shell containing plurality of inserts having recesses 22 shaped to receive the user's teeth.

Figure 1:
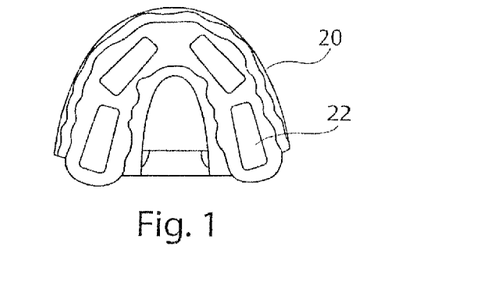
FIG. 1 is a top plan view of a mouthpiece portion of a device in accordance with the present disclosure.
Figure 2:
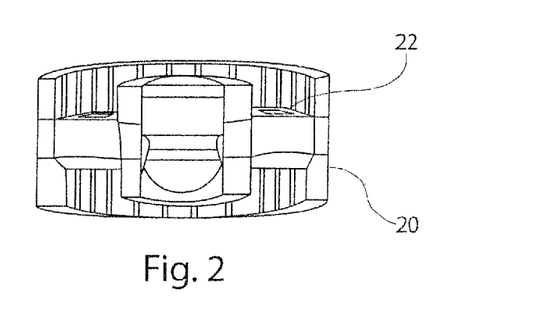
FIG. 2 is a rear view of the mouthpiece portion of FIG. 1.
Figure 3:
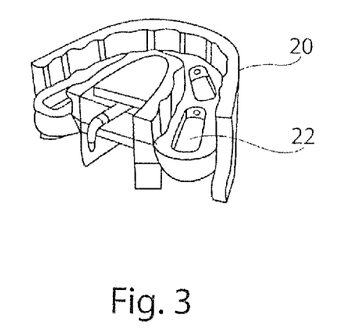
FIG. 3 is a perspective view thereof.

Mouthpiece 20 may be in the shape of a circular arc, an elliptical curve, a hyperbolic curve, a parabolic curve, a parallelogram or a trapezoid.

Figure 4:
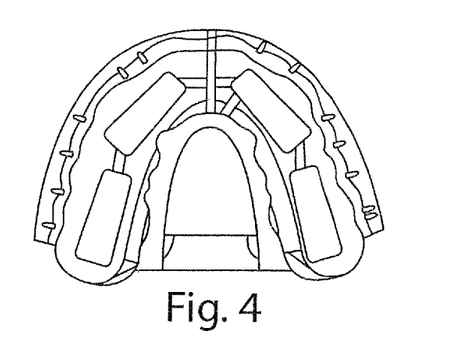
FIG. 4 is a view similar to FIG. 1, with external surfaces removed to show internal details.
Figure 5:
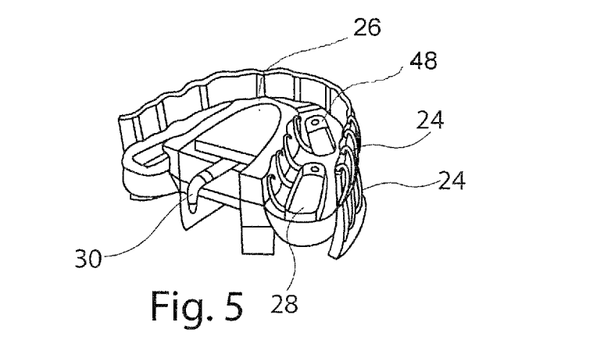
FIG. 5 is a view similar to FIG. 3, with external surfaces removed to show internal elements.
Figure 6:
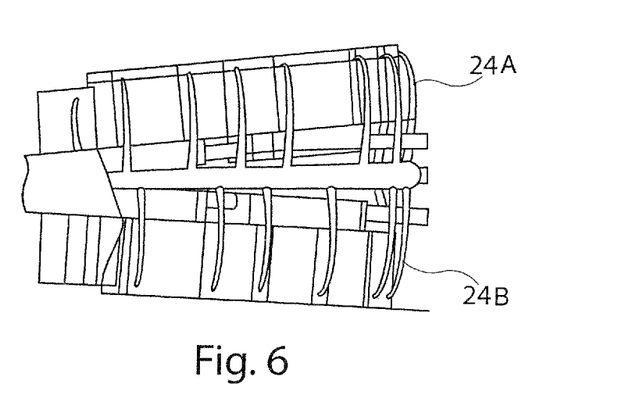
FIG. 6 is a right plan view with external surfaces removed to show internal detail.

Referring in particular to FIGS. 4-6, mouthpiece 20 comprises a plurality of brushes or picks 24 driven by a vibrator 26. As seen particularly in FIGS. 5 and 6, at least some of the picks 24 A, 24B, are located on the exterior walls of the mouthpiece and extend to clean the gums, tongue and roof of the mouth. Also, if desired, mouthpiece 20 may include a plurality of compartments 28 and/or tubes 30 for delivering dentifrice or other substance to the user's mouth.

Vibrator 26 preferably comprises a piezoelectric transducer or other high frequency vibrating device for generating vibrations, preferably, at ultrasonic frequency, to drive the brushes, and cause mild cavitation in the dentifrice to loosen soft plaque on the surface of the teeth and to transmit ultrasonic vibrations to adjacent tissue such as the gums, tongue and roof of the mouth. Vibrator 26 preferably is driven by a re-chargeable battery. Alternatively, mouthpiece 20 may be driven by ultrasonic pulses of water similar to ultrasonic tooth cleaning apparatus available commercially from WaterPik.

In one embodiment, the vibrator comprises a plurality of ultrasonic transducers having the same geometry offset from one another. In one embodiment, the ultrasonic transducers are linear and laid flat on the mouthpiece. In another embodiment the vibrators comprise a plurality of ultrasonic transducers electrically connected in series. In yet another embodiment, the vibratory comprises a plurality of ultrasonic transmitters electrically connected in parallel. In one embodiment the vibrator comprises a plurality of ultrasonic serially arranged transducers extending substantially parallel to one another and offset to one another. In yet another embodiment, the ultrasonic transmitter are oriented in the shape of a circular arc or in the shape of an elliptical curve, or a hyperbolic curve, a parabolic curve, a parallelogram or a trapezoid.

Figure 7:
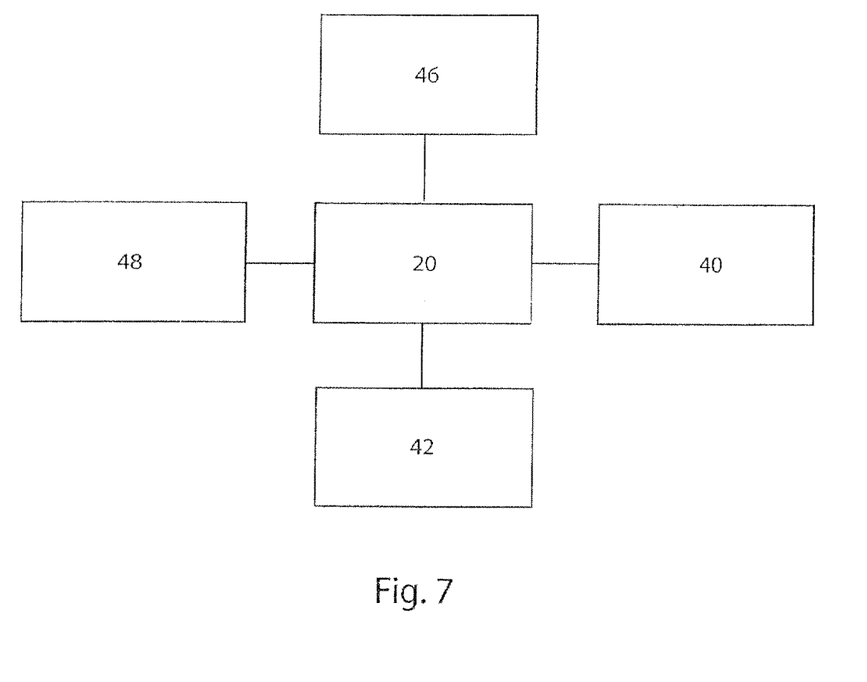
FIG. 7 is a diagrammatic flow diagram of an aspect of the present disclosure.
Figure 8:
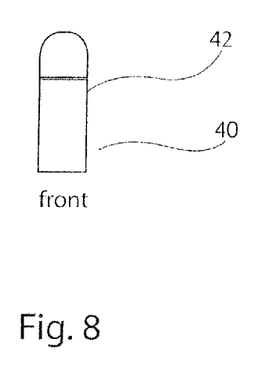
FIG. 8 is a front view of a supply unit element of the present disclosure.
Figure 9:
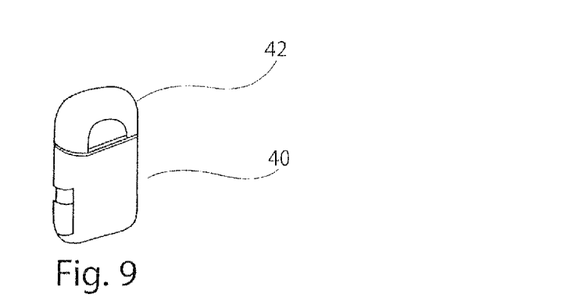
FIGS. 9-11 are respectively perspective view, side view and top view of the supply unit of FIG. 8.
Figure 10:
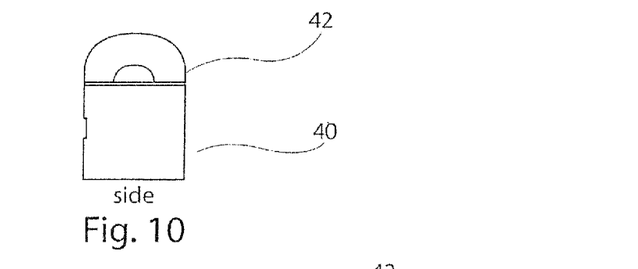
Figure 11:
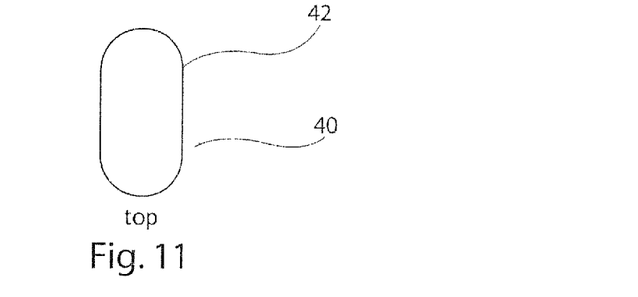

Referring also to FIG. 7, in a preferred embodiment, the mouthpiece may be connected to a display screen 40 which may comprise screens for displaying messages or graphically-rich content entertainment to the user while the user is brushing his or her teeth. The device also may contain a sensor or sensors 42 for measuring at least one physiological parameter which may include a salt component, temperature, moisture, pH, dehydration levels, blood oxygen levels, humidity or combinations thereof in the oral cavity. The device also may contain a flexible or wearable sensor 46 for real-time screening and/or diagnosis of medical conditions of the user or, if desired, may contain a disclosing solution for detecting plaque in the oral cavity using, for example color indicators conventionally used in dentistry, for detecting and identifying tooth plaque.

In yet another embodiment, the mouthpiece may include a light which may be internal or external for directing light towards the teeth and for sensing light reflected from the teeth for display on the display screen for providing feedback to the user.

The device also may comprise sensors to detect biological species in the breath.

In yet another embodiment, the mouthpiece may include a fluid-supply for supplying dentifrice or mouthwash or the like to the user, and also a drainage or suction device for draining excess fluid and saliva. Also if desired, the device may include compressed air and water for washing debris, scale and plaque from the teeth, gums, tongue and roof of the mouth.

Referring to FIGS. 8-11, in yet another embodiment of the disclosure, the system includes a cleaning device 40 to clean and sterilize the mouthpiece. Sanitation station 40 typically comprises a holder body 42 of a size to hold the device 20 in a cleaning solution. Holder device 42 may include ultrasonic vibratory for causing cavitation in the cleaning solution held therein. Cleaning device 40 also may include, for example, an ultraviolet light source 48 for sanitizing the mouthpiece 20.

Various changes may be made in the above description without departing from the spirit and scope of the invention. For example:

The cleaning elements could be removable and replaceable (i.e. new bristles) at some time or use interval, or the entire component could be replaced. Also, the mouthpiece could include tubing to flow liquids, as well as an "out" suction to remove liquids from the oral cavity. The device could be stand alone (i.e. with integrated battery) or connected to a power source or "base station". The base station could provide not only power, but also a supply of water (cold, warm or hot), as well as source of cleaning materials (i.e. toothpaste, fluoride containing or otherwise and or mouthwashes. In one embodiment, the base station could be manually filled with cleaning components, mouthwash, could be integrated with a "cartridge" which would pre-load the base station for one or more "brushing". If desired, the base station could be directly connected to hot and/or cold external water supply. The base station also could be a "docking" element for the mouth component, in which the oral contact portion it would be cleaned between every or some interval of time or number of "brushings", cleaning could include by chemical (i.e. alcohol), UV light or other mechanism.

The system also could have any number of washing cycles"—these could include but are not limited to a "pre-cycle" . . . in which for example a rinse with water or saline or fluoride type mouthwash of any number of varieties. This could be followed by "wash cycle" in which teeth and gums are cleaned by mechanical motion, and/or ultrasound, sonication or other mechanism post wash "rinse" which could include mouthwash or elements for example to enhance "whitening" of teeth or other options.

Portable systems could be provided without a base station, which would have the option of carrying cases (for travel). The cases could include recharging elements (battery or charging cord), washing component elements (i.e. cartridges) or beyond.

In summary the system would integrate multiple elements ranging from means to "fit" to the user, multiple, potential cleaning modalities, means to connect a base station which could supply various elements (rinse, cleaning pastes), and could be utilized in multiple potential cleansing cycles and temporalities.

The overall benefits would include faster, more effective teeth cleaning and gum health, reduced numbers of caries and other oral pathologies, ability to trace use, providing incentives and game-ification element.

The invention claimed is:

1. A dental device for cleaning user's teeth, gums, tongue and roof of the mouth of the user, comprising a mouthpiece shaped to fit or approximate the user's mouth, and to fit in the user's mouth, said device including one or a pore vibratory elements for vibrating portions of the device relative to the user's teeth, and/or gums, and including one or more brushes driven by the one or more vibratory elements, wherein at least some of the brushes are located on an exterior wall of the mouthpiece and extend to clean the gums, tongue and roof of the mouth of the user when the device is in use.

2. The device of claim 1, wherein the one or more vibratory elements comprises one or more ultrasonic transducers.

3. The device of claim 1, wherein the mouthpiece includes one or more tubular structures for delivering or removing a fluid to the user's mouth.

4. The device of claim 1, wherein the mouthpiece further includes an ultraviolet light source.

5. The device of claim 1, wherein the one or more vibratory elements is electrically driven.

6. The device of claim 5, wherein the one or more vibratory elements is battery driven.

7. The device of claim 1, wherein the mouthpiece further includes one or more sensors for measuring at least one physiological parameter of the user's mouth.

8. The device of claim 7, wherein the physiological parameter is selected from the group consisting of a salt component, temperature, moisture, pH, dehydration, blood oxygen level and humidity.

9. The device of claim 1, wherein the mouthpiece is configured to hold a disclosing solution for detecting plaque.

10. The device of claim 1, wherein the mouthpiece further includes a fluid supply for supplying dentifrice or mouthwash.

11. The device of claim 10, wherein the mouthpiece further includes a drainage or suction device for draining excess fluid and saliva.

12. The device of claim 1, where the mouthpiece is custom fitted to the user.

13. A dental device comprising a mouthpiece, shaped to fit or approximate the user's mouth, and to fit in the user's mouth, said device including one or more vibratory elements for vibrating portions of the device relative to the user's teeth and/or gums, and including one or more brushes driven by the one or more vibratory elements, wherein at least some of the brushes are located on an exterior wall of the mouthpiece and extend to clean the gums, tongue and roof of: the mouth of the user when the device is in use, and a cleaning device for cleaning and storing the mouthpiece between uses.

* * * * *

UNITED STATES PATENT AND TRADEMARK OFFICE
CERTIFICATE OF CORRECTION

Page 1 of 1

PATENT NO. : 10,478,273 B2
APPLICATION NO. : 14/912310
DATED : November 19, 2019
INVENTOR(S) : Daniel Kraft et al.

It is certified that error appears in the above-identified patent and that said Letters Patent is hereby corrected as shown below:

In the Claims

Claim 1, Column 5, Line 2 "one or a pore" should be --one or more--

Claim 12, Column 6, Line 13 "where the mouthpiece" should be --wherein the mouthpiece--

Signed and Sealed this
Tenth Day of March, 2020

Andrei Iancu
*Director of the United States Patent and Trademark Office*